United States Patent
Resnick

(10) Patent No.: US 10,657,221 B2
(45) Date of Patent: *May 19, 2020

(54) FILE SYSTEM FOR MEDICAL IMAGES AND DATA

(71) Applicant: Synaptive Medical (Barbados) Inc., Bridgetown (BB)

(72) Inventor: Jonathan Resnick, Toronto (CA)

(*) Notice: Subject to any disclaimer, the term of this patent is extended or adjusted under 35 U.S.C. 154(b) by 280 days.

This patent is subject to a terminal disclaimer.

(21) Appl. No.: 15/463,631

(22) Filed: Mar. 20, 2017

(65) Prior Publication Data
US 2017/0193162 A1 Jul. 6, 2017

Related U.S. Application Data

(63) Continuation of application No. 14/674,974, filed on Mar. 31, 2015, now Pat. No. 9,600,489.

(51) Int. Cl.

| | |
|---|---|
| *G06F 16/00* | (2019.01) |
| *G06F 19/00* | (2018.01) |
| *G06F 3/0484* | (2013.01) |
| *G06F 16/13* | (2019.01) |
| *G06F 16/58* | (2019.01) |
| *G06F 16/14* | (2019.01) |
| *G06F 16/182* | (2019.01) |
| *G06F 16/18* | (2019.01) |
| *G06F 3/0482* | (2013.01) |

(52) U.S. Cl.
CPC ........ *G06F 19/321* (2013.01); *G06F 3/04842* (2013.01); *G06F 16/13* (2019.01); *G06F 16/156* (2019.01); *G06F 16/182* (2019.01); *G06F 16/1847* (2019.01); *G06F 16/58* (2019.01); *G06F 16/5866* (2019.01); *G06F 3/0482* (2013.01)

(58) Field of Classification Search
CPC ...... G06F 16/13; G06F 16/156; G06F 16/182; G06F 16/1847; G06F 16/58; G06F 16/5866; G06F 19/321; G06F 3/0482; G06F 3/04842
See application file for complete search history.

(56) References Cited

U.S. PATENT DOCUMENTS 7,580,950 B2 * 8/2009 Kavuri ................. G06F 3/0605
8,120,613 B2 2/2012 Baumgart et al.
(Continued)

OTHER PUBLICATIONS

Marcus et al., "The extensible Neuroimaging Archive Toolkit" Neuroinformatics, vol. 5, (2007) p. 11-33.
(Continued)

*Primary Examiner* — Dinku W Gebresenbet

(57) ABSTRACT

The present invention is an improvement to a computer system for processing, storing and searching DICOM medical imaging objects and non-DICOM files. The improvement is the addition of a directory manager, a user interface and a search manager that allows users to define a hierarchy of directories that link to both DICOM and non-DICOM files. Contents of files are indexed, including metadata so they are searchable. The system automatically creates directories representing DICOM series and studies by analyzing metadata in DICOM image files DICOM devices can send DICOM data directly to directories in the file system using the DICOM protocol.

8 Claims, 3 Drawing Sheets

(56) References Cited

U.S. PATENT DOCUMENTS

| | | |
|---|---|---|
| 8,140,481 B2 | 3/2012 | Sato et al. |
| 8,935,431 B2 | 1/2015 | Oehme et al. |
| 2006/0242148 A1 | 10/2006 | Rothpearl et al. |
| 2009/0103789 A1* | 4/2009 | Danner ................ G06F 19/321 |
| | | 382/128 |
| 2009/0132285 A1 | 5/2009 | Jakobovits |
| 2009/0274384 A1* | 11/2009 | Jakobovits ............. G06F 16/51 |
| | | 382/254 |
| 2011/0191301 A1 | 8/2011 | Becker et al. |
| 2013/0325507 A1* | 12/2013 | Kuwayama ............ G16H 10/60 |
| | | 705/3 |
| 2014/0278530 A1 | 9/2014 | Bruce et al. |
| 2015/0058042 A1 | 2/2015 | Vrbicky |

OTHER PUBLICATIONS

Teaching File System (TFS), created by Medical Imaging Resource Center (MIRC): https://www.rsna.org/tfs.aspx, Copyright © 2014 Radiological Society of North America , pp. 1-2.

Box for Healthcare: Secure Healthcare Data & Storage & Sharing I Box, https://www.box.com/industries/healthcare- life-sciences/, © 2015 Box, pp. 1-3.

* cited by examiner

FILE SYSTEM FOR MEDICAL IMAGES AND DATA

FIELD OF THE INVENTION

The present invention relates generally to computer file systems, and more particularly to computer file systems that index and facilitate searching of standard imaging objects comprising medical image data formatted according to a standard format for storing medical imaging objects, such as the DICOM standard.

BACKGROUND OF THE INVENTION

Traditional Picture Archiving Communications Systems (PACSs) have evolved primarily to serve the needs of the clinical settings in which they are predominantly used. Other settings such as medical imaging research, teaching, or industry, when faced with the need to store and catalogue DICOM image data, have typically (a) stored images as DICOM files on a typical computer file system (e.g. Windows™ NTFS™), using directory structures as a means of organizing the data, or (b) attempted to adapt traditional PACS solutions, working within, or around, their limitations, or (c) built custom "homegrown" systems, typically supplementing elements of (a) and/or (b) with additional external database(s). Each of these approaches have drawbacks and limitations.

The standard file system storage approach has the advantage of flexibility, in that users can organize their data in directory structures of arbitrary design. However, there are various drawbacks to this approach. For example, the user can interact with the DICOM images only as opaque files. Users cannot "see" or interact with the hierarchical study-series-image structure of the data, or other meta-data encoded in the DICOM files, without having to open the files in a DICOM application. Also, the user cannot search for images of interest, except by browsing the directory structure or searching based on file name. Because the files are opaque to the file system, DICOM metadata is not indexed and hence cannot be used as a basis for search. Using this approach, it is difficult to centralize the system for shared access. Network file systems support shared access, but provide no means of coordinating file access to prevent or resolve update conflicts and maintain data integrity. Finally, there is no support for DICOM communication protocols, which limits the ability to integrate with other DICOM-enabled devices and applications.

Adapting a traditional PACS has the advantage that, unlike the file system approach, PACSs are DICOM aware. They support DICOM communication protocols, typically allowing some degree of interaction with the hierarchical study-series-image structure of the data and/or other meta-data encoded in the DICOM files, and supporting some basic search capabilities with respect to this metadata. Use of such a system also solves the problem of centralization for shared access. However, such an approach has several deficiencies.

PACSs limit the ability to organize and catalogue the data in arbitrary ways. The system organizes data to meet clinical needs, i.e., according to Patient and Study and Image identifiers. A corollary to this is that a given image can typically be stored exactly once in the system, because its identity is determined by its Image and Study identifiers. In non-clinical usage, this restriction is unnecessarily limiting, as there may be a need to store different copies of objects that share the same identifier.

Search capabilities offered by PACSs are typically limited to a very small subset of the DICOM metadata, which is selected for clinical relevance. A typical PACS might support searching by Patient ID, Patient Name, Study ID, Study Date, Study Description and Modality. The vast majority of the DICOM metadata is not indexed and hence cannot be used as a basis for search.

There is no ability to store native non-DICOM data in the system alongside DICOM data. With the file system approach, it is easy to add arbitrary (non-DICOM) files into a directory along with related image files, but storage of non-DICOM files isn't generally possible in a PACS, at least not without first encapsulating em into a DICOM container file.

Even PACSs that do support storage of encapsulated non-DICOM files do not typically support searches based on the content of these files. With the file system approach, typical operating systems (e.g. Windows™) tend to index the content of common file types (e.g. PDF), making it possible to search for files based on their content. In contrast, when a non-DICOM file is stored in a PACS (by encapsulating it into a DICOM container file), the file becomes opaque and its content is not searchable.

In such approaches, there is limited or no ability to "own" data. Because the PACS is designed for clinical use, the data typically resides in a single logical repository accessible to all users of the system. Ownership of individual pieces of data, either by individual users, or groups of users, is not possible.

DICOM communication may be the only way to import/export data to/from the PACS, which limits the ability to integrate it with applications that do not support DICOM communication.

SUMMARY OF THE INVENTION

In various examples, the present disclosure provides systems and methods, and improvements to systems and methods, for processing and storing DICOM medical imaging objects. The invention provides flexible storage, cataloguing and indexing of DICOM formatted medical imaging data to serve non-clinical or para-clinical use cases (e.g. research, teaching, industry) that are not well served by traditional PACSs designed for clinical use.

In some examples, the present disclosure provides an improvement to a computer system for processing and storing DICOM medical imaging objects. The computer system includes a computer processor, a user input device for receiving input from a user, a display device for displaying information to the user, and a non-volatile memory. The improvement is the addition of a directory manager, a user interface and a search manager, each of which is implemented by the processor. The associated functionality may be implemented by customizing the processor hardware or by software running on a programmable processor, for example.

The directory manager is configured to allow a user, via the user interface, to create and manage subdirectories. Each subdirectory is linked by a parent directory, the parent directory being either a root directory or another subdirectory. At least some of the directories are configured to be linkable to DICOM image files containing medical image data. The DICOM image files are formatted according to the DICOM standard format for storing medical imaging objects, and include metadata. At least some of the directories that are configured to be linkable to DICOM image files are further configured to also be linkable to non-DICOM files that are not formatted according to the DICOM standard.

The user interface is configured to receive a search request from the user via the user input device, and to display on the display device results of a search performed by a search manager according to the search request.

The search manager is configured to, in response to a search request, search the contents, including metadata, of both DICOM imaging objects and non-DICOM files linked by a directory specified in the search request. After performing a search, the search manager returns the results of the search request to the user interface.

In some preferred embodiments, each subdirectory is linked by exactly one parent directory. The user interface may also be further configured to display on the display device a representation of at least a portion of the hierarchy defined by links between the directories and the links from directories to the DICOM imaging objects and the non-DICOM files. The user may then be able to select a representation of one of the displayed non-DICOM files or DICOM imaging objects, causing the user interface to display information about the selected item on the display device. The user may further be able to specify a new subdirectory to be created by specifying a parent directory and a subdirectory name, causing the directory manager to create the new subdirectory linked by the parent directory, and causing the user interface manager to update the display to include the new subdirectory.

In some embodiments, every directory may be configured to link to both DICOM imaging objects and non-DICOM files.

In some embodiments, the user may be able to select a representation of one of the DICOM image files displayed by the user interface, causing the user interface to display the image stored in the selected DICOM image file and metadata associated with the image on the display device.

In some preferred embodiments, the directory manager may be further configured to receive and store in the memory a plurality of DICOM image files, each DICOM file containing metadata specifying a DICOM series to which the image belongs and a DICOM study to which the DICOM series belongs, so that, for each DICOM image file the directory manager is further configured to: (i) receive a specification of a destination directory; (ii) create a link to the DICOM image file in a series directory representing the DICOM series; (iii) create a link to the series directory in a study directory representing the DICOM study; and (iv) create a link to the study directory in the specified destination directory. Furthermore in such embodiments, at least one of the directories may be assigned a DICOM application entity title. In such embodiments, specifying the destination directory involves specifying the application entity title of one of the directories.

In some embodiments, the user interface may be further configured to receive keywords from the user for a specified file and the directory manager may be further configured to tag the specified file with those keywords as metadata.

In some examples, the present disclosure provides a method of indexing and searching multiple DICOM objects and non-DICOM files stored in a memory in a computer system having a network interface and a network address. The method is performed by a computer processor in the computer system. The method involves the creation of directories, each directory being linked by a parent directory. At least some of the directories are configured so that they are capable of linking to one or more DICOM image files and also to one or more non-DICOM files. The method further involves receiving and storing in the memory DICOM image files, each DICOM image file containing an image and DICOM metadata. The metadata specifies a DICOM series to which the image belongs and a DICOM study to which the DICOM series belongs. Then, for each DICOM image file: (i) a specification of a destination directory is received; (ii) a link to the DICOM image file in a series directory representing the DICOM series is created; (iii) a link to the series directory in a study directory representing the DICOM study is created; and (iv) a link to the study directory in the specified destination directory is created. The method further involves receiving and storing in the memory non-DICOM files, and for each non-DICOM file receiving a specification of a destination directory, and creating a link in the destination directory to the non-DICOM file. The method further involves indexing metadata contained in the DICOM image files and indexing content of non-DICOM files to create a search index. The method further involves receiving a search request from a user specifying a directory to be searched and a search query. In response to the search request, the indexed data of both DICOM image files and non-DICOM files linked by the specified directory is searched, and the results of the search are provided to the user.

In some embodiments of the method, the destination directory may be assigned a DICOM application entity title. In such embodiments, specifying the destination directory involves specifying the application entity title of the destination directory, the network address of the network interface and a port number.

Some embodiments of the method may further include a step of displaying on a display device a representation of at least a portion of the hierarchy defined by links between the directories, the DICOM image files and the non-DICOM files, and allowing the user to specify a directory to be searched by selecting one of the displayed directories. The user may be able to select a displayed representation of one of the files, in which case the method involves causing at least a portion of the contents of the selected file to be displayed. The method may further involve receiving a request to attach a non-DICOM file to a DICOM image file and then recording the attachment so that when a representation of the DICOM image file is displayed an indication that the non-DICOM file is attached to the DICOM image file is also displayed.

In some embodiments of the method, in response to the search request, the indexed data of all DICOM image files and non-DICOM files linked directly or indirectly by the specified directory may be searched.

In some examples, the present disclosure provides an improvement to a computer system. The computer system includes a computer processor, a user input device for receiving input from a user, a display device for displaying information to the user, and a non-volatile memory. The improvement is the addition of a directory manager, a user interface and a search manager, each of which his implemented by the processor. Each subdirectory is linked by a parent directory, the parent directory being either a root directory or another subdirectory. At least some of the directories are configured to be linkable to standard imaging objects comprising medical image data, which have been formatted according to a standard format for storing medical imaging objects. The standard imaging objects include metadata. At least some of the directories that are configured to be linkable to standard imaging objects are also configured to be linkable to non-standard files that are not formatted according to the standard format for storing medical imaging objects. The user interface is implemented by the processor and is configured to receive search requests from the user via the user input device. Upon receipt of the results of the search performed by the search manager according to the search request, the user interface displays the search results on the display device. The search manager is configured to, in response to a search request, search the contents, including metadata, of both standard imaging objects and non-standard files linked by a directory specified in the search request, and to return the results of the search request to the user interface.

In some examples, the present disclosure provides a computer system including a computer processor, a user input device for receiving input from a user, a display device for displaying information to the user, a non-volatile memory, a directory manager, a user interface and a search manager. The directory manager, user interface and search manager are all implemented by the processor, which may purpose-built custom hardware or be a programmable processor with software implementing some or all of the functionality of directory manager, user interface and search manager, for example. The directory manager creates and manages subdirectories. Each subdirectory is linked by a parent directory, the parent directory being either a root directory or another subdirectory. At least some of the directories are configured to be linkable to standard imaging objects comprising medical image data, the objects being formatted according to a standard format for storing medical imaging objects. The standard imaging objects include metadata. At least some of the directories that are configured to be linkable to standard imaging objects are further configured to also be linkable to non-standard files that are not formatted according to the standard format for storing medical imaging objects. The user interface is configured to receive search request from users via the user input device, and to display on the display device results of a search performed by a search manager according to such a search request. The search manager is configured to, in response to a search request, search the contents, including metadata, of both standard imaging objects and non-standard files linked by a directory specified in the search request, and to return the results of the search request to the user interface for display to the user. The computer system may also include a network interface for exchanging data over a network with devices connected to the network. The computer system further may also include an image data communications interface configured to receive standard imaging objects via the network interface using a standard protocol for exchanging medical imaging objects. In such embodiments, the image data communications interface is configured to (i) receive a standard imaging object from a device connected to the network configured to transmit standard imaging objects using the standard protocol, (ii) store the received standard imaging object in the memory, and (iii) link the received standard imaging object to a destination directory specified by the device. The image data communications interface may be further configured to transmit standard imaging objects via the network interface using the standard protocol for exchanging medical imaging objects. In such embodiments, the image data communications interface may allow the user to specify a particular standard imaging object linked by one of the directories, and to specify a device connected to the network configured to receive standard imaging objects using the standard protocol, thereby causing the image data communications interface to transmit the specified standard imaging object to the specified device using the standard protocol. The standard format for storing medical imaging objects may be the DICOM format for storing medical imaging objects, the standard imaging objects may then comprise DICOM image files, each DICOM image file containing an image and DICOM metadata specifying a DICOM series to which the image belongs and a DICOM study to which the DICOM series belongs. In such embodiments, the DICOM image file may be stored in the memory, a link to the DICOM image file may be created in a series subdirectory corresponding to the DICOM series, a link to the series subdirectory may be created in a study directory corresponding to the DICOM study, and a link to the study subdirectory may be created in a destination subdirectory. At least one of the directories may be assigned a DICOM application entity title, in which case specifying the destination directory by the device comprises specifying the application entity title of one of the directories.

Related inventions were described in PCT application no, PCT/CA2014/000482, which is hereby incorporated herein by reference in its entirety.

DESCRIPTION OF THE DRAWINGS

FIG. 3 depicts a computer system employing an embodiment of the invention, showing the major functional elements and showing external elements that the system may interact with.

DETAILED DESCRIPTION OF THE INVENTION

Figure 1:
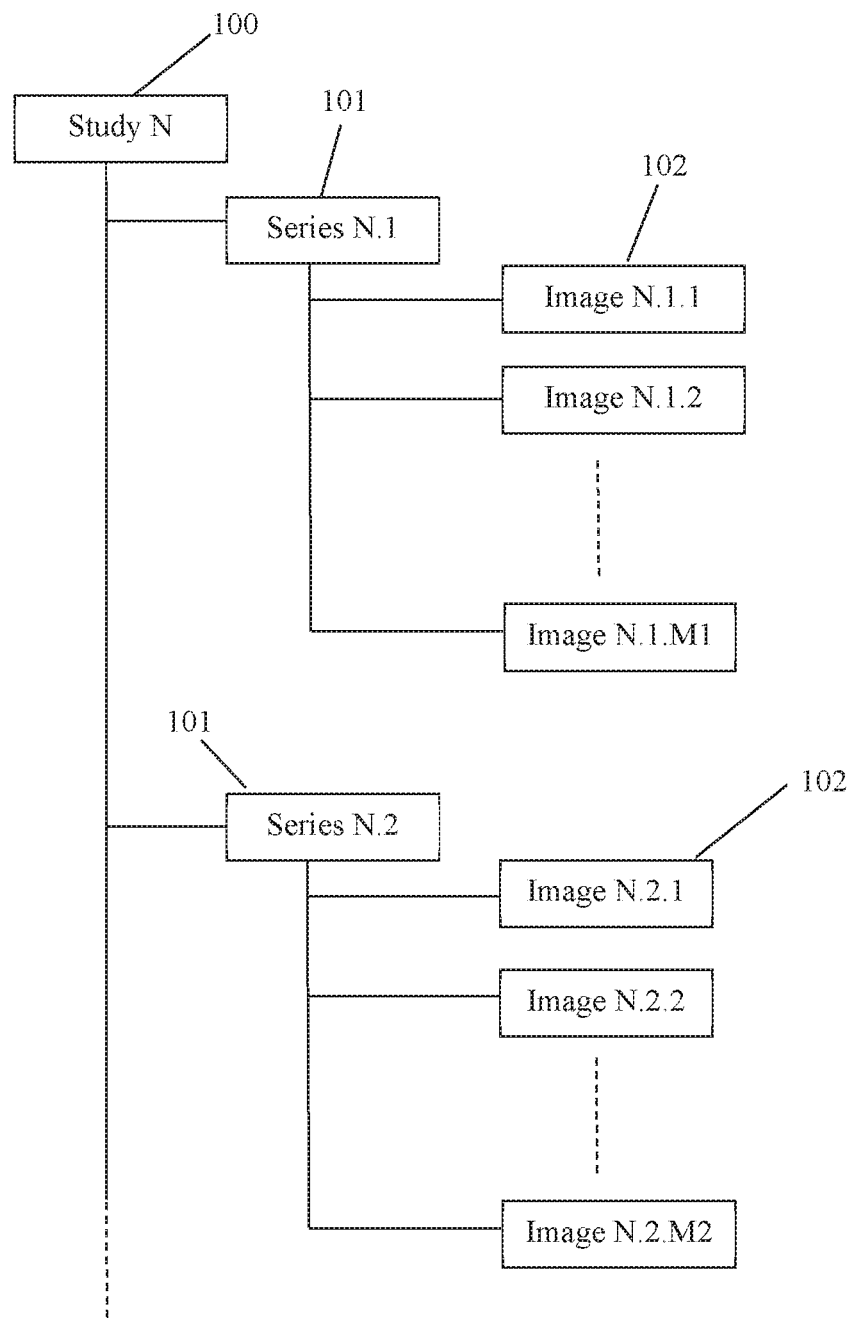
FIG. 1 depicts the structure of an example of a DICOM study, showing two series, each series having multiple images.

FIG. 1 depicts the structure of an example of a DICOM study, showing two series 101, 102 contained in the study. Series N.1 101 contains M1 images 102 identified as Image N.1.*i* for integers i from 1 to M1, where M1 is a positive non-zero integer. For example, if M1 is 10, then the tenth and last image in Series N.1 is Image N.1.10. Series N.2 101 contains M2 images 102 identified as Image N.2.*i* for integers i from 1 to M2, where M2 is a positive non-zero integer.

Each DICOM image 102 is contained in a DICOM image file, which file also includes DICOM metadata, including a specification of the series to which the image in the file belongs and a specification of the study to which the series belongs. From a set of image files, the study/series relationships like those depicted in FIG. 1 can be determined from the DICOM metadata in the DICOM image files.

The directory manager (DM) disclosed herein is configured to create and manage a hierarchical file system in which can be stored DICOM medical imaging objects as well as non-standard (or more accurately "non-DICOM") files that are not formatted according to the DICOM standard, such as text, word processor and spreadsheet files, as well as non-DICOM image and video files, for example. There is no requirement to first encapsulate non-DICOM files into a DICOM container file.

Figure 2:
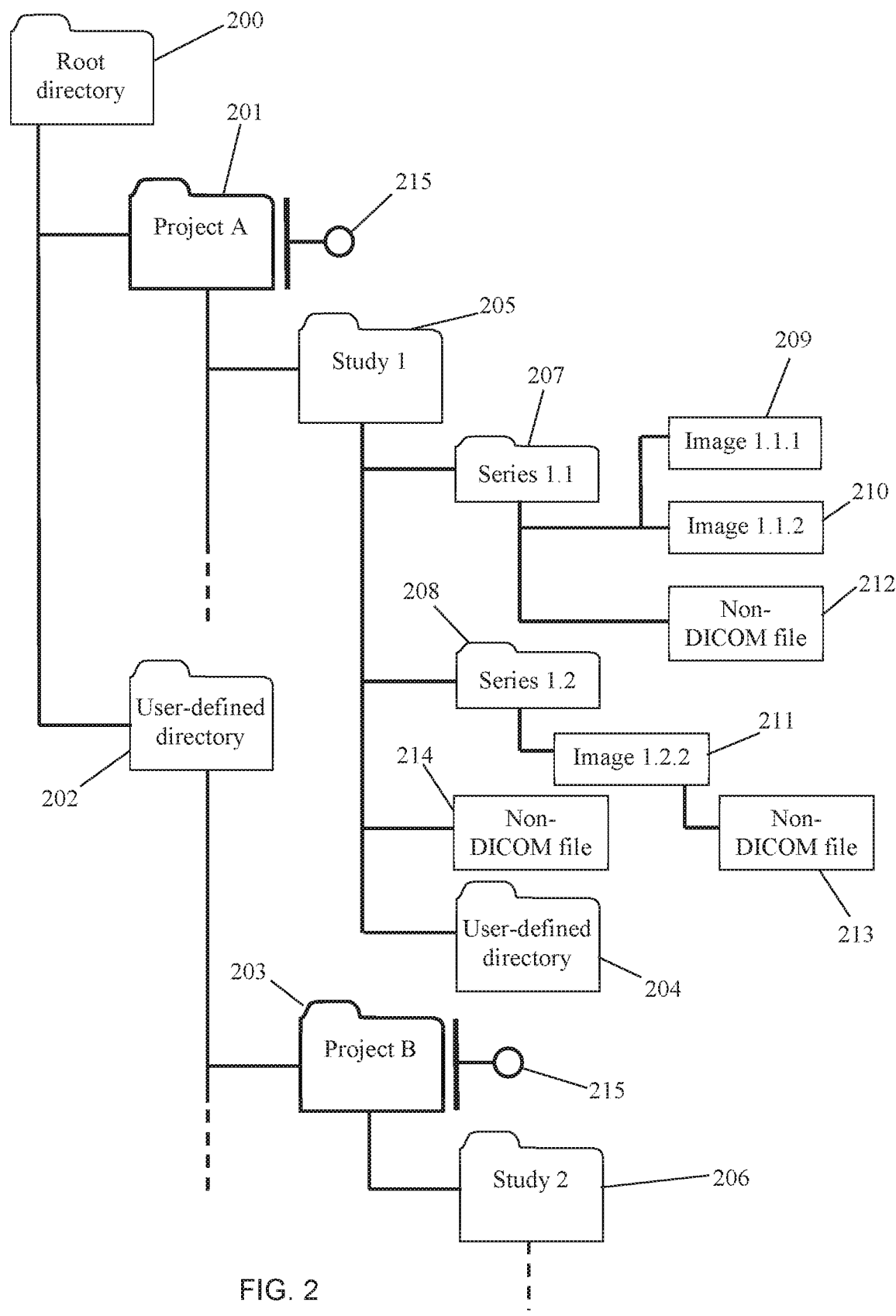
FIG. 2 shows a representation of files organized in a file system provided by an embodiment of the invention.

A file system generally defines one (or more) root directories that have no parent directory, such as the root directory 200 in FIG. 2. Directories that have a parent directory may optionally be referred to as subdirectories. Directories and subdirectories may alternatively be referred to as "folders" or "sub-folders". A directory is a special file in the file system that is configured so that it can store links to other directories (child directories) and/or to non-directory files, such as non-DICOM files and DICOM image files. Normally each subdirectory is linked by exactly one parent directory in order to avoid creating loops so that the file system is hierarchically tree-structured, with the non-directory files as leaves.

Non-directory files may be linked by one or more directories (i.e. multiple directories can have links to the same file without copies of the file being made). Generally when the last link to a file is deleted, the file itself is deleted (e.g. the space in memory that was used by the file is made available for use in storing new files in the file system). The DM may also support making actual copies of files, so that different files with the same contents may be linked by different directories. In such a case, changes made to one copy would not affect the other copies. The DM may give the user the option when copying a file of either creating a separate copy in another directory or of simply linking the same file to the other directory.

In a preferred embodiment, the DM may allow the user to request that a copy of a file be made in a directory, and initially make a link in the destination directory to the specified file, so that an actual copy of the file contents is not made. Then if the user makes a change to the file, at that point the DM creates a separate copy that is then linked to the destination directory so that the original copy remains unchanged. In this way disc space is minimized by avoiding allocating space to redundant copies of files.

A depiction of a portion of a file system created by an embodiment of a DM is depicted in FIG. 2. Non-directory files are depicted as rectangles. A key aspect of the DM is that when a DICOM image file is stored in the file system, the image file is automatically linked by a series directory corresponding to the series that the image contained in the image file is part of, as indicated by the DICOM metadata in the DICOM image file. The series directory may be given the name of the series. Similarly, each series directory is automatically linked by a study directory corresponding to the study that the image contained in the image file is part of, as indicated by the DICOM metadata in the DICOM image file.

For example, in the file system depicted in FIG. 2, the user has created root directory 200, and has also created two subdirectories linked by the root directory 200, being named Project A 201 and User-defined directory 202. Then DICOM image files 209, 210, 211 have been stored in the Project A directory 201. The DM has automatically extracted the relevant metadata from the image files to determine that Image 1.1.1 209 and Image 1.1.2 210 are part of Series 1.1 which is part of Study 1, and that Image 1.1.2 is part of Series 1.2, which is also part of Study 1. If a directory did not exist for Series 1.1 when Image 1.1.1 was received, then at that point the Series 1.1 subdirectory 207 is automatically created by the DM and the image file is linked by the Series 1.1 subdirectory 207. If the Series 1.1 subdirectory 207 already existed, then a link to the image file is created in the Series 1.1 subdirectory 207. Similarly, if a directory did not exist for Study 1 when Image 1.1.1 was received, then at that point the Study 1 subdirectory 205 is automatically created and linked by the Project A directory 201, and the Series 1.1 subdirectory 207 is linked by the Study 1 subdirectory 205. If the Study 1 subdirectory 205 already existed, then a link to the Series 1.1 subdirectory 207 is created in the Study 1 subdirectory 205.

The same process was repeated for Image 1.1.2 210 and Image 1.2.2 211, resulting in the creation of the Series 1.2 subdirectory 208 which is linked by the Study 1 subdirectory 205.

A key aspect of the DM is that a user can add native format non-DICOM files to directories such as study and series directories. For example, in FIG. 2 a user has added non-DICOM file 212 to the Series 1.1 subdirectory 207, and has added non-DICOM file 214 to the Study 1 subdirectory 205. A user-defined directory 204 has also been created by the user and linked by the Study 1 subdirectory 205. This user-defined directory 204 could have other non-DICOM files linked by it.

The DM may provide various mechanisms for a user to view and manage the file system and the files. For example, when the user selects a particular directory, such as the root directory 200 shown in FIG. 2, the DM may display a portion of the directories and files linked by the root directory 200 in a tree-like depiction, such as that shown in FIG. 2. Alternatively or additionally, the DM may display a hierarchy of directories on one pane, and then the files (including any directories) in an adjacent pane for one of the directories displayed in the first pane. This may work similarly to well-known file system user interfaces, such as provided by Windows™ Explorer™ in the Microsoft Windows™ operating systems, where the user can expand and contract the depiction of the directories by clicking on directories or associated controls.

After the DM has displayed a portion of a representation of the file system (such as that depicted in FIG. 2) to the user, the user may be able to perform various operations on the file system. For example, the user may be able to move or copy additional DICOM and non-DICOM files to various depicted directories. The user may be able to create new directories by selecting a parent directory and providing a new subdirectory name, which subdirectory may be designated to be a "DICOM directory". For the purposes of this disclosure a DICOM directory is simply a directory that has been so designated for the purpose of allowing DICOM communication by associating the directory with an application entity title, as described below.

The user may be able to select a file to be opened by a default handler for the type of file. For example, if the user opens a DICOM image file, the image may be displayed by an image viewer along with some of the DICOM metadata. If a user opens a word processor file, the DM may launch the word processor used to create the file so that the user can edit the file.

In some embodiments, the DM also allows the user to attach non-DICOM files to DICOM image files, such as the non-DICOM file 213 which has been attached to Image 2.2 211 as shown in FIG. 2. This may be useful, for example, to link diagnostic notes about a particular image to the image file. Where such notes are, for example, relevant to an entire series, then such notes may better be saved in a non-DICOM file linked by the series subdirectory, such as the non-DICOM file 212 which is linked by the Series 1.2 subdirectory 207, and which may contain notes about both Image 1.1.1 209 and Image 1.1.2 210.

DM supports both individual and group ownership of data. Each directory in the system is owned by either a user or group account, and access to the contents of that directory may be restricted accordingly.

Figure 3:
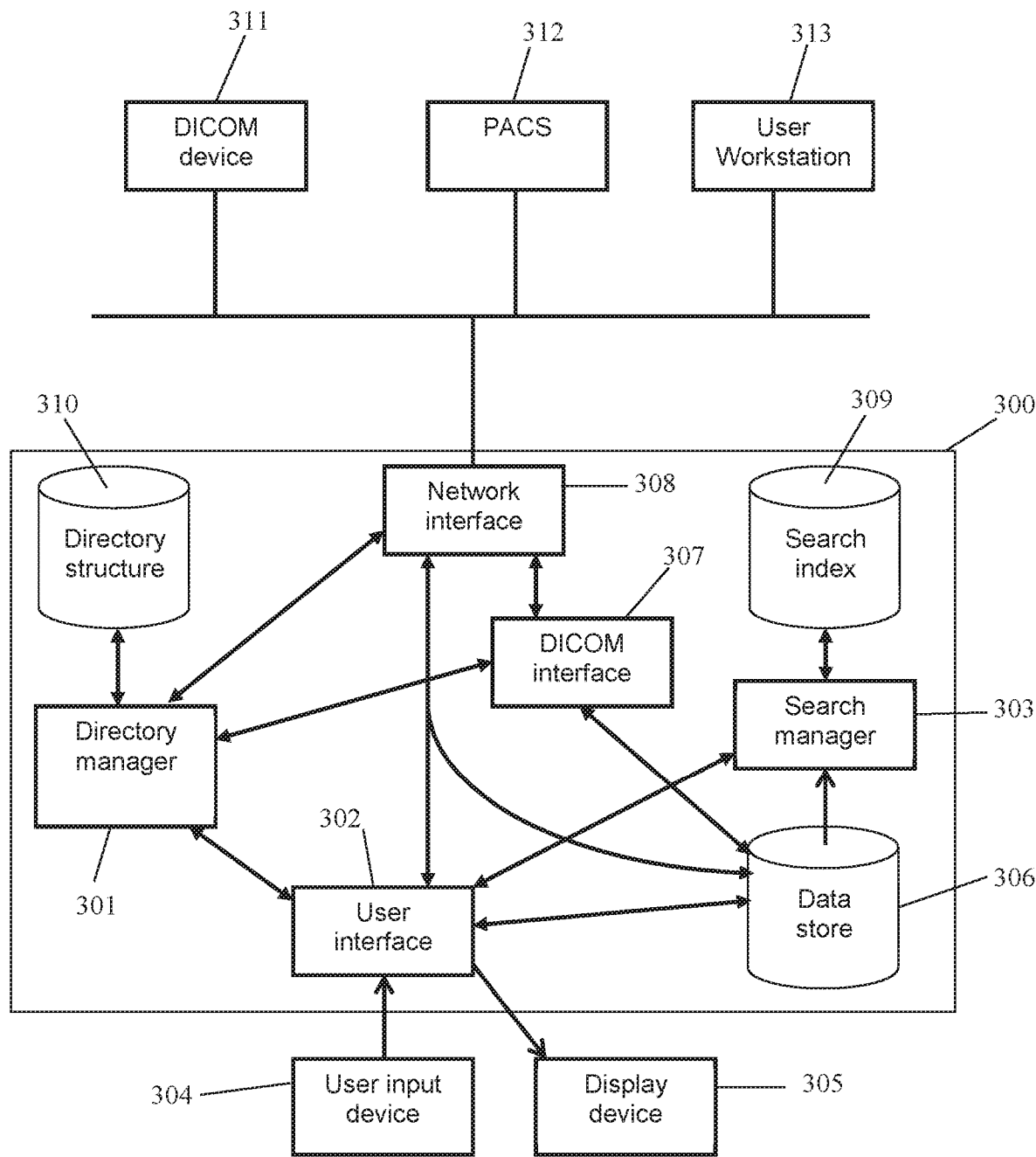

FIG. 3 depicts a computer system 300 employing an embodiment of the invention, showing the major functional elements and showing external elements that the system may interact with. The computer system 300 receives input from a user via a user input device 304, which may for example include a keyboard and a mouse, and presents information to the user via a display device 305, such as an LCD screen. The computer system 300 has a network interface 308, such as an Ethernet interface, to attach to a network having other devices connected to it, such as a Picture Archiving and Communications System (PACS) 312, other DICOM devices 311, and user workstations 313. Such user workstations 313 may provide equivalent capability for a user to interact with the computer system 300 as does the user input device 304 and display device 305.

The computer system 300 includes four key functional units, a directory manager 301, a user interface 302, a search manager 303 and a DICOM interface 307. These may be implemented by purpose-built custom hardware in the form of one or more custom computer chips, or may be implemented by software running on one or more computer processors, or any suitable combination of such approaches, for example. In a preferred, embodiment, the directory manager 301, user interface 302, search manager 303 and DICOM interface 307 are implemented by software running on one or more programmable computer processors.

The directory manager 301 implements the functions of the DM described above, storing the directory, file and link information in a directory structure database 310. The files themselves, such as DICOM image files, are stored in a data store 306, such as one or more hard drives. The user interface 302 is configured to receive search requests from users via the user input device 304 and to display on the display device 305 information to users, such as search results produced according to a search request. The search manager is configured to receive search requests from a user via the user interface 302. The search requests are requests to search the contents, which may include any or all metadata, of both standard DICOM imaging objects and non-DICOM files contained in the directory structure 310 created and maintained by the directory manager 301. A search request may specify a particular directory so that all files linked by that directory are to be searched. This may be limited to files linked directly by the directory, or extend to all files linked indirectly to the directory via one or more intermediate subdirectories. A search request generally includes one or more keywords to be searched for, and may specify particular fields (such as the modality in DICOM metadata) in which to search for particular keywords, with or without wildcard characters in the keywords.

The search manager 303 indexes the contents of non-DICOM files in a search index 309, including any metadata, and also indexes DICOM metadata in the DICOM files. Preferably, a relatively large subset of DICOM metadata is indexed, making it possible for users to search for images of interest using attributes that would not have been indexed by a system designed for clinical use. Furthermore, the DICOM meta-data indexing mechanism is extensible, making it possible to index all DICOM metadata, or subsets thereof.

Data is stored on a central server, such as in the depicted data store 306, accessible to all users of the system (provided the user has been granted the requisite access rights) via a web browser or other HTTP client via the network or via the local user input/output devices 304, 305. A locking mechanism coordinates multi-user access in order to prevent update conflicts and ensure data integrity. For example, multiple researchers may have links to a common analysis file so that each may edit and update the file so that everyone else sees the updates when they open the file. In some embodiments, the locking mechanism may only ensure that a second user cannot modify a file while a first user is in the process of downloading it.

The computer system 300 may include a DICOM interface 307 that facilitates communication of the computer system 300 with DICOM devices 311, such as PACSs 312, connected to the same network as the computer system 300. The DICOM interface 307 manages directories designated by a user to be DICOM directories so that each DICOM directory appears to other devices on the network to be a DICOM device. A specific DICOM application entity title is assigned to each such DICOM directory, for example, by the user entering the application entity title via the user interface 302. The external DICOM devices can address a DICOM directory by the combination of the application entity title, the network address of the network interface 308, and a TCP port number. Each DICOM directory is then effectively a separately addressable DICOM device, as conceptually indicated in FIG. 2 by the connectors 215 associated with the Project A directory 201 and the Project B directory 203. A DICOM client connected to the network can then send studies directly to a specific directory in the DM, and can also query and retrieve the contents of DM DICOM folders using the DICOM protocol. This is implemented by a portion of the DICOM interface 307 that listens for DICOM traffic addressed to the network address of the network interface 308 with a known TCP port number that indicates the traffic is DICOM traffic. The application entity title, in combination with the network address and TCP port, uniquely identifies a DICOM directory in the DM.

In addition to DICOM communication, data can be imported/exported to/from the DM by means of an HTTP interface, facilitating possibilities for integration with applications that do not support DICOM communication (software library support for DICOM communication, as a general purpose protocol, is far more ubiquitous than for DICOM communication).

Generally, a computer, computer system, computing device, client or server, as will be well understood by a person skilled in the art, includes one or more than one computer processor, and may include separate memory, and one or more input and/or output (I/O) devices (or peripherals) that are in electronic communication with the one or more processor(s). The electronic communication may be facilitated by, for example, one or more busses, or other wired or wireless connections. In the case of multiple processors, the processors may be tightly coupled, e.g. by high-speed busses, or loosely coupled, e.g. by being connected by a wide-area network.

A computer processor, or just "processor", is a hardware device for performing digital computations. A programmable processor is adapted to execute software, which is typically stored in a computer-readable memory. Processors are generally semiconductor based microprocessors, in the form of microchips or chip sets. Processors may alternatively be completely implemented in hardware, with hard-wired functionality, or in a hybrid device, such as field-programmable gate arrays or programmable logic arrays. Processors may be general-purpose or special-purpose off-the-shelf commercial products, or customized application-specific integrated circuits (ASICs). Unless otherwise stated, or required in the context, any reference to software running on a programmable processor shall be understood to include purpose-built hardware that implements all the stated software functions completely in hardware.

While some embodiments or aspects of the present disclosure may be implemented in fully functioning computers and computer systems, other embodiments or aspects may be capable of being distributed as a computing product in a variety of forms and may be capable of being applied regardless of the particular type of machine or computer readable media used to actually effect the distribution.

At least some aspects disclosed may be embodied, at least in part, in software. That is, some disclosed techniques and methods may be carried out in a computer system or other data processing system in response to its processor, such as a microprocessor, executing sequences of instructions contained in a memory, such as ROM, volatile RAM, non-volatile memory, cache or a remote storage device.

A non-transitory computer readable storage medium may be used to store software and data which when executed by a data processing system causes the system to perform various methods or techniques of the present disclosure. The executable software and data may be stored in various places including for example ROM, volatile RAM, non-volatile memory and/or cache. Portions of this software and/or data may be stored in any one of these storage devices.

Examples of computer-readable storage media may include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

Furthermore, at least some of the methods described herein may be capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer usable instructions may also be in various forms, including compiled and non-compiled code.

At least some of the elements of the systems described herein may be implemented by software, or a combination of software and hardware. Elements of the system that are implemented via software may be written in a high-level procedural language such as object oriented programming or a scripting language. Accordingly, the program code may be written in C, C++, J++, or any other suitable programming language and may comprise modules or classes, as is known to those skilled in object oriented programming. At least some of the elements of the system that are implemented via software may be written in assembly language, machine language or firmware as needed. In any case, the program code can be stored on storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein.

While the teachings described herein are in conjunction with various embodiments for illustrative purposes, it is not intended that the teachings be limited to such embodiments. On the contrary, the teachings described and illustrated herein encompass various alternatives, modifications, and equivalents, without departing from the described embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

Where, in this document, a list of one or more items is prefaced by the expression "such as" or "including", is followed by the abbreviation "etc.", or is prefaced or followed by the expression "for example", or "e.g.", this is done to expressly convey and emphasize that the list is not exhaustive, irrespective of the length of the list. The absence of such an expression, or another similar expression, is in no way intended to imply that a list is exhaustive. Unless otherwise expressly stated or clearly implied, such lists shall be read to include all comparable or equivalent variations of the listed item(s), and alternatives to the item(s), in the list that a skilled person would understand would be suitable for the purpose that the one or more items are listed.

The words "comprises" and "comprising", when used in this specification and the claims, are to used to specify the presence of stated features, elements, integers, steps or components, and do not preclude, nor imply the necessity for, the presence or addition of one or more other features, elements, integers, steps, components or groups thereof.

What is claimed is:

1. A computer system for organizing and accessing DICOM files and non-DICOM files, the computer system comprising:
   (a) a computer processor;
   (b) a user input device for receiving input from a user;
   (c) a network interface;
   (d) a display device for displaying information to the user;
   (e) a directory manager implemented by the processor for creating and managing directories, each directory being linked by exactly one parent directory, a plurality of the directories being configured to be linkable to DICOM files, each DICOM file comprising a medical image and being formatted according to the DICOM standard, each DICOM file containing metadata specifying a DICOM series to which the image belongs and a DICOM study to which the DICOM series belongs, at least some of the plurality of the directories further being configured to also be linkable to native format non-DICOM files that are not formatted according to the DICOM standard format for storing medical image files;
   (f) a user interface implemented by the processor configured to display on the display device, in response to a selection by the user, a representation of at least a portion of the files and hierarchy defined by links between the directories and the links from directories to the DICOM files and the non-DICOM files, and configured to, in response to a selection by the user of one of the representations of files, display at least a portion of the contents of the file corresponding to the selected representation; and (g) a DICOM interface configured to listen for DICOM requests addressed to a network address of the network interface, wherein one or more of the directories is a DICOM-enabled directory having a DICOM application entity title, and the directory manager is further configured to receive DICOM requests from the DICOM interface, each DICOM request including a DICOM application entity title specifying one of the DICOM-enabled directories and including a plurality of DICOM files, so that, in response to the DICOM request, for each DICOM file, the directory manager creates a link to the DICOM file in a series directory representing the DICOM series, creates a link to the series directory in a study directory representing the DICOM study, and creates a link to the study directory in the specified DICOM-enabled directory.

2. The computer system of claim 1, wherein the system is configured to enable the user to select one of the representations of one of the DICOM files displayed by the user interface, and in response to the selection the user interface displays the image stored in the selected DICOM file and metadata associated with the image on the display device.

3. The computer system of claim 1, wherein the system is configured to enable the user to select a representation of one of the displayed files, and in response to the selection of a representation of one of the files the user interface displays information about the file represented by the selected representation.

4. The computer system of claim 1, wherein the system is configured to enable the user to specify a new directory to be created by specifying a parent directory and a directory name, and in response to the specification the directory manager creates the new directory linked by the parent directory, and the user interface manager updates the display to include the new directory.

5. A method of organizing and accessing DICOM files and non-DICOM files stored in a memory in a computer system having a computer processor, a network interface, a network address and a DICOM interface configured to listen for DICOM requests addressed to the network address, the method being performed by the computer processor, the method comprising the steps of:

(a) creating a plurality of directories, each directory being linked by exactly one parent directory, a plurality of the directories being configured to be linkable to DICOM files, each DICOM file comprising a medical image and being formatted according to the DICOM standard, each DICOM file containing metadata specifying a DICOM series to which the image belongs and a DICOM study to which the DICOM series belongs, at least some of the plurality of the directories further being configured to also be linkable to native format non-DICOM files that are not formatted according to the DICOM standard format for storing medical image files, wherein one or more of the directories is a DICOM-enabled directory having a DICOM application entity title;

(b) displaying, in response to a selection by a user, a representation of at least a portion of the files and hierarchy defined by links between the directories and the links from directories to the DICOM files and the non-DICOM files;

(c) in response to a selection by the user of one of the representations of files, displaying at least a portion of the contents of the file corresponding to the selected representation; and (d) receiving DICOM requests from the DICOM interface, each DICOM request including a DICOM application entity title specifying one of the DICOM-enabled directories and including a plurality of DICOM files, and (e) in response to each DICOM request, for each DICOM file, creating a link to the DICOM file in a series directory representing the DICOM series, creating a link to the series directory in a study directory representing the DICOM study, and creating a link to the study directory in the specified DICOM-enabled directory.

6. The method of claim 5 further including the step of receiving from the user a selection of one of the displayed representations of one of the DICOM files, and in response to the selection, displaying the image stored in the selected DICOM file and metadata associated with the image.

7. The method of claim 5 further including the step of receiving from the user a selection of one of the displayed representations of one of the files, and in response to the selection displaying information about the file represented by the selected representation.

8. The method of claim 5 further including the step of receiving from the user a specification of a new directory to be created by specifying a parent directory and a directory name, and in response to the specification the directory manager creating the new directory linked by the parent directory, and updating the display to include the new directory.

\* \* \* \* \*